United States Patent [19]

Hahn

[11] Patent Number: 5,733,362

[45] Date of Patent: *Mar. 31, 1998

[54] SYNERGISTIC BACTERICIDE

[75] Inventor: Lothar Hahn, Wachtendonk, Germany

[73] Assignee: Troy Corporation, Florham Park, N.J.

[21] Appl. No.: 759,103

[22] Filed: Dec. 2, 1996

Related U.S. Application Data

[60] Provisional application No. 60/008411 Dec. 8, 1995.

[51] Int. Cl.$^6$ .......................... A01N 31/00; A01N 33/00; A01N 47/12
[52] U.S. Cl. .......................... 106/18.33; 106/18.32; 106/18.34; 106/18.35; 422/28; 424/78.09; 424/401; 424/405; 514/373; 514/479; 514/731; 514/844
[58] Field of Search .................. 106/15.05, 18.32, 106/18.33, 18.34, 18.35; 424/78.09, 401, 405; 422/28; 514/372, 373, 478, 479, 731, 844

[56] References Cited

U.S. PATENT DOCUMENTS

| | | | |
|---|---|---|---|
| 4,276,211 | 6/1981 | Singer et al. | 106/18.32 |
| 4,552,885 | 11/1985 | Gabriele et al. | 514/316 |
| 4,708,959 | 11/1987 | Shroot et al. | 514/373 |
| 4,844,891 | 7/1989 | Rosen et al. | 514/389 |
| 4,866,081 | 9/1989 | Ito et al. | 514/367 |
| 4,964,892 | 10/1990 | Hsu | 514/372 |
| 5,147,884 | 9/1992 | Diehl et al. | 514/365 |
| 5,156,665 | 10/1992 | Sherba et al. | 514/364 |
| 5,332,765 | 7/1994 | Lorentzen et al. | 523/122 |
| 5,374,478 | 12/1994 | Lorentzen et al. | 106/15.05 |

FOREIGN PATENT DOCUMENTS

| | | |
|---|---|---|
| 2053807 | 11/1993 | Canada . |
| 0 492 811 | 7/1992 | European Pat. Off. . |
| 6016506 | of 1994 | Japan . |
| 7133206 | of 1995 | Japan . |
| WO 93/08690 | 5/1993 | WIPO . |
| WO 96/17724 | 6/1996 | WIPO . |

OTHER PUBLICATIONS

Chemical Abstract No. 125:188221 which is an abstract of a Polish Journal article by Marcinski et al entitled "Stability Of An Isothiazoline biocide in water–oil emulsions" 75(8) 299–301 (1996).

Zeneca Biocides, Ein wasserlösliche Isothiazolinon–Derivat zur Konservierung von Dispersionen, (Feb. 1993), pp. 105–108.

"Chemical Abstracts", vol. 119, No. 16, abstract No. 162410m (Oct. 1993).

*Primary Examiner*—Anthony Green
*Attorney, Agent, or Firm*—Banner & Witcoff, Ltd.

[57] ABSTRACT

This invention is directed to a bactericidal composition which comprises a synergistic mixture of 2-methyl-4,5-trimethylene-4-isothiazoline-3-on; 3-iodo-2-propynyl butyl carbamate and 2-phenoxyethanol.

19 Claims, No Drawings

SYNERGISTIC BACTERICIDE

This application claims the benefit of U.S. provisional application Ser. No. 60/008,411 filed on Dec. 8, 1995.

BACKGROUND OF THE INVENTION

1. Field of the Invention

This invention is directed to a bactericidal composition containing 2-methyl-4,5-trimethylene-4-isothiazoline-3-on, 3-iodo-2-propynyl butyl carbamate and 2-phenoxyethanol.

2. Description of Related Art

Polymer dispersions or aqueous latex paints containing polyvinyl alcohol, polyacrylates or vinylpolymers, thickener solutions containing cellulose derivatives, kaolin suspensions and metal working fluids, are prone to degradation by the action of objectionable microorganisms, particularly bacteria, which can significantly impair the usefulness of such compositions. Such degradation produces changes in pH values, causes gas formation and the formation of objectionable odors, and may produce changes in rheological properties. Foremost among the bacterial pests are the Pseudomonas species, while enterobacteriaceae, such as Proteus and Enterobacter, also often cause significant problems.

An enormously wide variety of materials has been identified for treating such compositions, all of which, to varying degrees, are effective at retarding or preventing the growth of and accompanying destruction caused by microbes. Such biocidal materials include halogenated compounds, organo-metallic compounds, quaternary ammonium compounds, phenolics, metallic salts, heterocyclic amines, formaldehyde donors, organo-sulfur compounds and the like. Formulated products are protected against microbial attack by the inclusion of such biocidal additives. Many of these materials have deficiencies related to toxicity, pH and temperature sensitivity, and compatibility that limit their utility.

Among the substances used by the prior art for the suppression of unwanted bacterial growth, formaldehyde-generating or donor compounds, such as iminozolidinylurea, diazolidinylurea, and hexahydrotriazine, have proven effective. The use of formaldehyde-generating substances as preservatives, however, has been subject to considerable criticism in recent years due to toxicological concerns. Another potential class of preserving agents are those which contain chlorine in their chemical structure. These compounds also are considered troublesome from an ecological point of view.

The mixture of the isothiazoline derivatives 5-chlorine-2-methyl-4-isothiazoline-3-on and 2-methyl-4-isothiazoline-3-on (Kathon CG, a trademark of Rohm & Haas) also has been effective in some applications. Unfortunately, its effectiveness is reduced at a pH above 7.5, and at a pH above 8.0, inactivation can occur (Wallh äuβer, Sterilization, Disinfection, Preservation Practice, Fourth Edition, Thieme Verlag Stuttgart, 1988, pp. 532 and 533). Since most aqueous paint formulations latices) are adjusted to a pH of between about 8.5 and 9.5, the use of this preserving agent is problematic in such applications. As a result, there is a need for preserving agents which can be used at low dosages, which are not based on the release of formaldehyde, which do not contain chlorine in their molecular structure, which do not lose their effectiveness at a pH over 8.5 and which are compatible with aqueous formulations.

3-iodo-2-propynyl butyl carbamate, hereinafter also referred to as IPBC, is a well known and highly active broad spectrum fungicide. In addition to its fungicidal activity, IPBC also has been associated with algaecidal activity. In this regard, Great Britain Patent 2,138,292 and U.S. Pat. Nos. 4,915,909 and 5,082,722 contain such disclosures. IPBC does not itself exhibit any significant bactericidal activity.

IPBC has been found to perform in a synergistic fashion with a variety of adjuvants. In particular, U.S. Pat. No. 4,844,891 (with formaldehyde donors); U.S. Pat. No. 5,128,372 (with N-4-dihydroxy-α-oxobenzene-ethanimidoyl chloride); U.S. Pat. No. 5,134,158 (with 3,4-dichloro-1,2-dithiol-3-one); U.S. Pat. No. 5,134,160 (with 2,2-dibromo-2-nitrilopropionamide); U.S. Pat. No. 5,147,890 (with N,N-dimethyl-N'-phenyl-(N'-fluorodichloromethylthio) sulfamide); U.S. Pat. No. 5,147,891 (with phenyl-(2-cyano-2-chlorovinyl) sulfone); U.S. Pat. No. 5,162,343 (with sodium 2-pyridinethiol-1-oxide); U.S. Pat. No. 5,219,875 (with 1,2-benzisothiazolon-3-one) and U.S. Pat. No. 5,428,050 (with N-[1,3-bis(hydroxymethyl)-2,5-dioxo-4-imidazolidinyl]-N,N'-bis(hydroxymethyl) urea) each describe the use of IPBC in binary synergistic mixtures. Japanese application 92-0197639 describes a composition containing IPBC and 2-octyl-isothiazoline-3-on as having improved anti-mold activity. Canadian 2,053,807 indicates that a certain range of proportions of 2-n-octyl-4-isothiazolin-3-one and IPBC exhibits synergy in controlling the growth of bacteria.

BRIEF DESCRIPTION OF THE INVENTION

In accordance with the present invention, it has now surprisingly been found that a combination of 2-methyl-4,5-trimethylene-4-isothiazoline-3-on (MTI), 3-iodo-2-propynyl butyl carbamate (IPBC) and 2-phenoxyethanol (PE) has a pronounced, unforeseeable synergistic effectiveness as a bactericide in aqueous formulations. These individual components when used in combination as a ternary mixture in quantities that, if used alone or in a binary mixture would be ineffective, show excellent bactericidal activity. 3-iodo-2-propynyl-butyl carbamate, for example, is generally regarded as only being effective as a fungicide (company brochure, "Troysan Polyphase P-100 - Fungicide," Troy Chemical, Oct. 1994). The prior art discloses the use of 2-phenoxyethanol for preserving cosmetic agents, but at a concentration of 0.5–1.0% (5000–10,000 ppm) (K. H. Wallhäuβer, Sterilization, Disinfection, Preservation Practice, Fourth Edition, Georg Thieme Verlag Stuttgart, N. Y. 1988, p. 480). This was confirmed by tests with a metal working fluid (Emol-o-grind 151 E/1) which showed that 2-phenoxyethanol did not exhibit any bactericidal effect at concentrations of 0.3 to 0.5%. PE generally is used in combination with other more active bactericides or fungicides such as imidazolinuim urea, formaldehyde, 1,2-dibromo-2,4-decyanobutane, dehydroacetate or sorbic acid. The literature also indicates that the substance 2-methyl-4,5-trimethylene-4-isothiazoline should be used in an amount of at least 0.005 to 0.01% (50–100 ppm) for sufficient preservation of dispersion paints (latices) and polymer dispersions (Paint & Lacquer, 99, 1993, p. 105). It is the discovery of the present invention that aqueous formulations containing a mixture of these three ingredients, in an amount of less than 1% by weight and generally between about 0.15 and 0.25% by weight of the aqueous formulation, protects the formulation from bacterial attack.

DETAILED DESCRIPTION OF THE INVENTION

The present invention is directed to a composition suitable for controlling unwanted bacterial growth in aqueous formulations. The composition comprises a synergistic mixture of 2-methyl-4,5-trimethylene-4-isothiazoline-3-on (MTI), 3-iodo-2-propynyl butyl carbamate (IPBC) and 2-phenoxyethanol (PE). The weight ratio of IPBC to MTI in the composition preferably falls within the range of about 0.5 to 5 and most often is between about 1 and 3. On the basis of these three active ingredients, the synergistic composition preferably contains from at least about 90% PE, more preferably at least about 95% PE, up to about 98% PE, with the balance being the mixture of MTI and IPBC. The composition can be provided as a concentrate containing only these three active ingredients for addition to an aqueous formulation to be protected against bacterial attack or for formulating other compositions such as dispersions or emulsions; or can be further diluted, such as with a solvent/liquid selected from water and organic solvents, including common water-compatible organic solvents.

The quantity of the inventive composition to be added to an aqueous formulation and accordingly, the quantities of the respective components, necessary for achieving the required bactericidal effect can vary in treated compositions, depending on the susceptibility of materials in the aqueous formulation to be protected prior to bacterial attack. Quantities of the combination of ingredients required for adequate protection of the treated aqueous formulations will often be in the range of 0.15 to 0.26%, where the proportion of the 3-iodo-2-propynyl-butyl carbamate and the 2-methyl-4,5-trimethylene-4-isothiazoline-3-on components is, in total, between about 0.0035 and 0.007% by weight of the composition, with the balance being the 2-phenoxyethanol.

Treated compositions of the present invention, which also provide protection against fungus, generally contain between 10 and 100, preferably between 50 and 100 percentage by weight solids, and can be converted to the usual formulations, such as solutions, emulsions, suspensions, and pastes. The form selected depends ultimately on the intended use. Uniform distribution of the synergistic, bactericidally effective composition of the present of the invention in the treated composition should be ensured in any event. Water dilutable formulations and concentrates containing the biocidal composition of the present invention are produced in the usual manner, e.g., using solvents, emulsifiers and dispersants.

The composition of the present invention has utility for retarding microbial growth in cooling towers, paints, metal working fluids, marine antifoulant coatings, spray washes, swimming pools, coatings, fabric, leather, paper, wood, cosmetic formulations and other personal care products, fuel systems, therapeutic pharmaceutical formulations and the like, and specifically in aqueous systems.

Depending on the intended use, additional bactericides and/or fungicides also can be added to the treated mixtures.

The bactericidal composition of the present invention is effective against a large number of bacteria, for example, *Pseudomonas aeruginosa*, *Pseudomonas putida*, *Pseudomonas oleovorans*, *Pseudomonas fluorescence*, *Aeromonas hydrophila*, *Citrobacter freundii*, *Enterobacter aerogenes*, *Klebsiella pneumonise*, *Proteus vulgaris*, *Proteus mirabils*, *Proteus rettgeri*, *Serratia marcescens*, and *Micrococcus flavus*.

Based on the weight of the formulated product to be protected, especially aqueous systems, the composition of the present invention is added in an amount of about 0.15 to 0.26 weight %. It is preferred that the quantities of the respective components of the composition be distributed in the system to be protected as follows:

| | |
|---|---|
| 2-methyl-4,5-trimethylene-4-isothiazoline-3-on | 0.001–0.003% |
| 3-iodo-2-propynyl-butyl-carbamate | 0.0025–0.005% |
| 2-phenoxyethanol | 0.15–0.25% |

Generally, a treated formulation is prepared from a highly concentrated composition of the active ingredients either by appropriate dilution or by adding an appropriate amount of the concentrate to a formulation. As noted above, the useful range for the active composition in the final formulation for the noted end use systems is about 0.1% to 0.3%.

Compositions of the present invention can generally be formulated by mixing the IPBC and MTI active ingredients in a selected proportion with PE as a liquid vehicle for dissolving or suspending the other active components. The vehicle may also contain a diluent, an emulsifier and a wetting-agent.

When preparing the ternary formulations of the present invention for specific applications, the composition may also be provided with other adjuvants conventionally employed in compositions intended for the specifically intended applications. Such adjuvants include organic binding agents, additional fungicides, auxiliary solvents, processing additives, fixatives, plasticizers, UV-stabilizers or stability enhancers, water soluble or water insoluble dyes, color pigments, siccatives, corrosion inhibitors, antisettlement agents, anti-skinning agents, and the like.

The following examples are presented to illustrate and explain the invention. Unless otherwise indicated, all references to parts and percentages are based on weight.

The present invention is directed to synergistic mixtures of MTI, IPBC, and PE. A synergistic effect is generally regarded as the response of a mixture of two or more components that is greater than the sum of the response of the individual components. A mathematical approach for assessing synergy, as reported by F. C. Kull, P. C. Elisman, H. D. Sylwestrowicz and P. K. Mayer, in *Applied Microbiology*, 9:538 (1961) can be applied to ternary mixtures using the following equation:

$$\text{Synergistic Index (SI)} = Q_a/Q_A + Q_b/Q_B + Q_c/Q_C$$

where:

$Q_a$=the quantity of component A used in a ternary mixture that gives the desired effect (such as no bacterial growth), $Q_A$=the quantity of component A which when used alone gives the desired effect, $Q_b$=the quantity of component B used in a ternary mixture that gives the desired effect, $Q_B$=the quantity of component B which when used alone gives the desired effect, $Q_c$=the quantity of component C used in a ternary mixture that gives the desired effect, $Q_C$=the quantity of component C which when used alone gives the desired effect.

If the SI for a composition is less than one (<1), that composition exhibits synergistic behavior.

EXAMPLES

The following examples illustrate the unforeseeable synergism of the combination of the present invention compared with the effectiveness of the individual substances.

For testing the effectiveness of the inventive compositions for suppressing unwanted bacterial growth, a styreneacrylate dispersion paint having a pH of about 9.2 was used. After mixing the individual components and the inventive mixture with 200 g of the dispersion paint in plastic beakers, the respective test samples were inoculated with $10_8$ KBE (colony-forming units) of bacteria per ml of paint. The bacterial suspension used to inoculate the test samples consisted of the following bacterial species, which were previously cultivated on and harvested from a nutrient agar: *Pseudomonas aeruginosa, Pseudomonas putida, Proteus rettgeri, Aeromonas hydrophila* and *Serratia marcescons*. After inoculation with the mixed bacteria culture, the test samples were sealed with foil and incubated for seven days at 30° C. To better assess the duration of effectiveness of the inventive mixture, compared with the individual components, the test samples were reinoculated with the mixed bacterial culture on three additional occasions at seven-day intervals and further incubated at 30° C. Portions of the test samples were subsequently transferred on bacteria-counting agar to Petri dishes in order to assess the bactericide and bacteriostatic effectiveness of the respective treatment compositions. Cultivation of the agar plates took place at 30° C. over a period of 72 hours. The bacterial growth on the agar plates was assessed according to the following schedule:

0=no bacterial development (very good effectiveness)

1=low bacterial development (good effectiveness)

2=bacterial development observed but inhibited to a large extent (acceptable effectiveness)

3=more noticeable bacterial growth (noticeable effectiveness; however, no longer sufficient)

4=significant bacterial growth (low effectiveness)

5=strong bacterial growth (totally ineffective).

The results of bacteriostatic and bactericide effectiveness of mixtures of 2-methyl-4,5-trimethylene-4-isothiazoline-3-on (MTI), 3-iodo-2-propynyl-butyl carbamate (IPBC) and phenoxyethanol (PE), in comparison with the effectiveness of the respective individual components after four inoculations with $10^8$ KBE (colony-forming units) of the mixed bacterial culture per milliliter of the dispersion paint, are reported below.

| Substance | Assessment of Effectiveness |
|---|---|
| MTI 0.001% + IPBC 0.005% + 2-phenoxyethanol 0.2% (EXAMPLE 1) | 0 |
| MTI 0.0015% IPBC 0.0025% + 2-phenoxyethanol 0.2% (EXAMPLE 2) | 0 |
| MTI 0.003% | 4 |
| MTI 0.0015% | 5 |
| MTI 0.001% | 5 |
| IPBC 0.01% | 5 |
| IPBC 0.005% | 5 |
| IPBC 0.0025% | 5 |
| 2-phenoxyethanol 0.25% | 4 |
| 2-phenoxyethanol 0.2% | 5 |
| 2-phenoxyethanol 0.15% | 5 |

These results show that the bactericide and bacteriostatic effectiveness of the mixture is considerably greater than the effectiveness of the individual components, which were generally not effective even in increased application concentrations.

In particular, these results and the information available from the literature show that (1) PE must be used in an amount of usually over 1% to obtain satisfactory bactericidal activity (thus $Q_A=1\%$); (2) IPBC has no significant bactericidal effect even when used in an amount of 0.2% (thus $Q_B \geq 0.2\%$); and finally (3) MTI is said to be effective in an amount as low as 0.005% (in comparison, our tests showed efficacy of MTI against bacteria in the styreneacrylate dispersion paint system at a level of 0.006%) (thus $Q_c=0.005\%$). Applying these values, together with the two inventive examples reported in the table above, to the formula reported above for determining synergy one determines the following:

EXAMPLE 1: SI=0.2/1.0+0.005/0.2+0.001/0.005

EXAMPLE 2: SI=0.2/1.0+0.0025/0.2+0.0015/0.005=0.5125

Both SI values are less than 1, thus under the recognized criteria for synergy referenced above, both compositions exhibit synergistic behavior.

While certain specific embodiments of the invention have been described with particularity herein, it will be recognized that various modifications thereof will occur to those skilled in the art and it is to be understood that such modifications and variations are to be included within the preview of this application and the spirit and scope of the appended claims.

What is claimed is:

1. A composition suitable for controlling unwanted bacterial growth comprising a synergistic mixture of 2-methyl-4,5-trimethylene-4-isothiazoline-3-on (MTI), 3-iodo-2-propynyl-butyl carbamate (IPBC) and 2-phenoxyethanol (PE).

2. The composition of claim 1 wherein the weight ratio of IPBC to MTI is within a range of about 0.5 to 5.

3. The composition of claim 2 wherein the weight ratio of IPBC to MTI is within a range of about 1 to 3.

4. The composition of claim 1 which, on the basis of the mixture of MTI, IPBC and PE, contains from about 90% PE to about 98% PE.

5. The composition of claim 1 which, on the basis of the mixture of MTI, IPBC and PE, contains from about 95% PE to about 98% PE.

6. The composition of claim 2 which, on the basis of the mixture of MTI, IPBC and PE, contains from about 90% PE to about 98% PE.

7. The composition of claim 3 which, on the basis of the mixture of MTI, IPBC and PE, contains from about 95% PE to about 98% PE.

8. An aqueous formulation protected against bacterial growth containing a bactericidal effective amount of a synergistic mixture of 2-methyl-4,5-trimethylene-4-isothiazoline-3-on (MTI), 3-iodo-2-propynyl-butyl carbamate (IPBC) and 2-phenoxyethanol (PE).

9. The aqueous formulation of claim 8 containing 2-methyl-4,5- trimethylene-4-isothiazoline-3-on in an amount of 0.001% to 0.003% by weight, 3-iodo-2-propynyl-butyl carbamate in an amount of 0.0025% to 0.005% by weight and 2-phenoxyethanol in an amount of 0.15% to 0.25% by weight.

10. The aqueous formulation of claim 8 wherein the mixture has a weight ratio of IPBC to MTI within a range of about 0.5 to 5.

11. The aqueous formulation of claim 10 wherein the weight ratio of IPBC to MTI is within a range of about 1 to 3.

12. The aqueous formulation of claim 10 containing said mixture in an amount of about 0.15% to 0.26% by weight.

13. The aqueous formulation of claim 11 containing said mixture in an amount of about 0.15% to 0.26% by weight.

14. The aqueous formulation of claim 12 wherein said mixture contains from about 90% PE to about 98% PE.

15. The aqueous formulation of claim 13 wherein said mixture contains from about 95% PE to about 98% PE.

16. A method for controlling unwanted bacterial growth in an aqueous formulation, comprising adding to said formulation a bactericidal effective amount of a synergistic mixture of 2-methyl-4,5-trimethylene-4-isothiazoline-3-on, 3-iodo-2-propynyl-butyl carbamate and 2-phenoxyethanol.

17. The method of claim 16 wherein said mixture is added to said aqueous formulation in an amount of about 0.15% to about 0.26% by weight.

18. The method of claim 16 wherein said aqueous formulation contains 2-methyl-4,5-trimethylene-4-isothiazoline-3-on in an amount of 0.001% to 0.003% by weight, 3-iodo-2-propynyl-butyl carbamate in an amount of 0.0025% to 0.005% by weight and 2-phenoxyethanol in an amount of 0.15% to 0.25% by weight.

19. The method of claim 18 wherein said aqueous formulation is selected from a dispersion paint, a metal working fluid, a marine antifoulant coating, a spray wash, a swimming pool additive, or a cosmetic formulation.

* * * * *